United States Patent [19]
Carver, Jr. et al.

[11] Patent Number: 5,907,240
[45] Date of Patent: May 25, 1999

[54] METHOD AND APPARATUS FOR CELL DIFFERENTIATION BY MEASURING APPARENT CELL SIZE, MEMBRANE INTEGRITY AND INTRACELLULAR COMPLEXITY

[75] Inventors: Edward Lawrence Carver, Jr.; David Charles DeCava, both of Oxford, Conn.

[73] Assignee: CDC Technologies, Inc., Oxford, Conn.

[21] Appl. No.: 08/854,377

[22] Filed: May 12, 1997

[51] Int. Cl.$^6$ .................................................. G01N 27/07
[52] U.S. Cl. ........................................ 324/71.1; 324/71.4
[58] Field of Search ................................ 324/71.1, 71.4, 324/692; 377/10, 11, 12; 422/72, 82.01, 82.02; 436/63, 65, 151; 73/861.41, 865.5

[56] References Cited

U.S. PATENT DOCUMENTS

| | | | |
|---|---|---|---|
| 3,836,849 | 9/1974 | Coulter et al. | 324/71.1 |
| 3,973,194 | 8/1976 | McMorris et al. | 324/71.1 |
| 4,298,836 | 11/1981 | Groves et al. | 324/71.1 |
| 4,368,423 | 1/1983 | Liburdy | 324/692 |
| 4,374,644 | 2/1983 | Armstrong | 324/71.4 |
| 4,472,506 | 9/1984 | Liburdy | 436/63 |
| 4,525,666 | 6/1985 | Groves | 324/71.1 |
| 4,535,284 | 8/1985 | Groves et al. | 324/71.1 |
| 4,760,328 | 7/1988 | Groves | 324/71.1 |
| 4,775,833 | 10/1988 | Roos et al. | 324/71.1 |
| 4,891,575 | 1/1990 | Kogo et al. | 324/71.1 |
| 4,972,137 | 11/1990 | Dunstan et al. | 324/71.1 |
| 5,187,673 | 2/1993 | Carver, Jr. et al. | 702/21 |
| 5,380,491 | 1/1995 | Carver, Jr. et al. | 422/73 |

OTHER PUBLICATIONS

Bull, Brian S., "On the Distribution of Red Cell Volumes", *Blood*, vol. 31, No. 4, pp. 503–515, Apr.1994.

Hoffman, R.A. and W.B. Britt, "Flow–System Measurment of Cell Impedence Properties", *The Journal of Histochemistry and Cytochemistry*, vol. 27, No. 1, pp. 234–240, 1979. month unavailable.

Kachel, V., "Basic Principles of Electrical Sizing of Cells and Particles and Their Realization in the New Instrument "Metricell"", *The Journal of Histochemistry and Cytochemistry*, vol. 24, No. 1, pp. 211–230, 1976. month unavailable.

Lief, R.C.; S. Schwartz; C.M. Rodriques; L. Pell–Fernandes; M. Groves; S.B. Leif; M. Cayer and H. Crews, "Two–Dimensional Impedance Studies of BSA Buoyant Density Separated Human Erythrocytes", *Cytometry*, vol. 6, pp. 13–21, 1985. month unavailable.

Zimmermann, U.; G. Pilwat and F. Rieman, "Dielectric Breakdown of Cell Membranes", *Biophysical Journal*, vol. 14, pp. 881–898, 1974. month unavailable.

*Primary Examiner*—Diep N. Do
*Attorney, Agent, or Firm*—Cummings & Lockwood

[57] ABSTRACT

A method and apparatus are provided for differentiating cells in an automated particle analyzer, such as for use in hematological analysis, by measuring apparent cell size (or volume), membrane integrity and intracellular complexity ("voltaic fragility"). The cells are suspended in a selected reagent mixture including an electrolytic fluid, such as diluent, and if necessary, one or more membrane-modifying agents are selected and mixed in relative quantities in order to selectively alter the membrane structure (i.e., the membrane integrity) of certain cells and thereby enhance cell discrimination. A predetermined dc voltage is applied across a sensing orifice to thereby create a dc electric field within and around the orifice, and the reagent mixture is passed through the center of the orifice. The magnitude of the change in current flowing through dc electric field is measured in response to the passage of each of a plurality of cells therethrough, and based on the measured change, a signal is generated for each cell which is indicative of the apparent size (or volume), membrane integrity and intracellular complexity of that cell. A visual display, such as an alphanumeric and/or graphical display, is then generated based on the signals facilitating differentiation of the cells.

20 Claims, 4 Drawing Sheets

METHOD AND APPARATUS FOR CELL DIFFERENTIATION BY MEASURING APPARENT CELL SIZE, MEMBRANE INTEGRITY AND INTRACELLULAR COMPLEXITY

FIELD OF THE INVENTION

The present invention relates to methods and apparatus for particle analysis, such a hematological analysis, and more particularly, to such methods and apparatus wherein the particles are suspended within an electrolytic fluid and the suspension is passed through a sensing orifice, a voltage is applied across the orifice, and electrical signals are generated indicative of the size and/or internal structure of the particles.

BACKGROUND OF THE INVENTION

Automated apparatus and methods for particle analysis, such as hematological analysis, typically pump a sample containing the particles suspended in a dispersion through a particle analyzer which detects differences in electrical, optical, chemical or other characteristics of the particles, and generates signals having characteristics relating to the differences. The signals are in turn transmitted to a processor for determining the parameters of the particle distributions.

Automated hematological analysis typically involves mixing within a cuvette or other mixing vessel a whole blood sample with several reagent-mixture components, such as diluent, and frequently one or more membrane-modifying agents, to create a reagent mixture which facilitates cell discrimination and identification. The reagent mixture is then pumped from the cuvette through the particle analyzer which detects the size and/or "opacity" of the blood cells by electrical and/or optical differences. The blood cells are detected or counted for a period of time sufficient to gather data for analysis, and data points are then stored and analyzed in a processor. The data may then be displayed in the form of a two-dimensional or three-dimensional histogram.

For many years, cell and particle counting and measuring instruments have measured the electrical resistance of cells or other particle suspensions in order to probe their structure and composition and in turn identify and discriminate among the subpopulations within a sample suspension. The early Coulter Counter™ instruments, sold by Coulter Electronics, Inc., operated upon the well-known principle of particle and cell measurement whereby a sample suspension is passed through a sensing orifice, a low-level dc voltage is applied across the orifice, and the change in impedance caused by the passage of the particles through the electric field of the orifice is measured to indicate the apparent particle size or volume.

Later developed instruments have provided information relating not only to particle size, but also characteristics due to the composition and nature of the particle material. Accordingly, these instruments have the capability to distinguish between cells of identical size having different intracellular characteristics, or other particles of identical size made of different materials. U.S. Pat. No. 3,836,849 shows one such instrument which generates particle sensing fields within the sensing orifice by means of both a dc current source and a radio frequency ("rf") current source, and in turn generates two or more interrelated output signals from the passage of each particle through the sensing orifice. A typical cell is composed of a thin, non-conducting outer cell membrane surrounding a cytoplasm containing other cell structure, such as a nucleus. Accordingly, the outer cell membrane functions as an insulator with respect to the relatively low level dc field, but is shorted out and is electrically "invisible" at the rf frequency. Thus, while all of the low-level dc current goes around the cell, some of the rf current goes through it. Accordingly, the resistance parameter detected in response to the dc field is the low-frequency conductivity depending only on, and indicative of the relative volume of the cell. The resistance parameter detected in response to the rf field, on the other hand, is the high-frequency conductivity determined by the resistivity of the cell interior as well as the relative volume. In an attempt to analogize the phenomenon to optical analysis, the ease with which the rf current will pass through a particle has been called "electrical transparency" or simply "transparency" of the particle; whereas the ability of the particle to impede the rf current has been called its "opacity".

The '849 patent further recognizes that different types of particles may exhibit the same or substantially the same opacity, and therefore suggests chemical treatment of select particles in order to alter their opacity and thereby facilitate in distinguishing between such particles having the same opacity.

One of the drawbacks of this type of prior art instrument is that it requires both dc and rf current sources, and in turn requires processing and analysis of at least two interrelated signals in order to provide an indication of both cell size and interior cell structure (also referred to as "intracellular complexity"). Accordingly, the additional costs of the rf source and related signal-processing electronics can render these instruments relatively expensive in comparison to those requiring a dc source only.

U.S. Pat. Nos. 4,368,423 and 4,472,506 to Liburdy show an apparatus and method for determining cell membrane dielectric breakdown in order to establish lymphocyte tumor cell cytotoxicity and the presence of actual tumor cells. Liburdy defines "dielectric breakdown" as occurring at the breakdown or breakpoint voltage whereby the lymphocyte cell membrane has undergone dielectric collapse and cell electrical resistivity has been markedly reduced. Liburdy recognizes that the breakdown voltage is directly related to the fluidity of the cell membrane and that lymphocyte cells which are cytotoxic possess decreased cell membrane fluidity. Liburdy's apparatus and method are therefore directed to determining cell membrane dielectric breakdown in order to establish lymphocyte tumor cell cytotoxicity as well as the presence of tumor cells. Liburdy draws the cells through a port within an electric field exposure tube, and a variable voltage source/amplifier is used to incrementally increase the voltage applied across the port and to the cells passing therethrough. The voltage source is set to stop at select intervals between 0 and 100 volts as the lymphocytes are drawn through the tube, a frequency histogram is acquired at each voltage exposure and stored, and the average voltage pulse height is plotted against the applied voltage to determine the breakdown profile of the lymphocyte cells.

One of the drawbacks of Liburdy's approach is that it is difficult and costly to construct a system that will take repeated and accurate measurements at each of the voltage increments. In addition, the cells are continuously drawn through the orifice and therefore different groups of cells are tested at each voltage increment, thus further increasing the likelihood of obtaining inconsistent and/or inaccurate test results. Because the system is dynamic, the flow conditions may likewise not be the same at each voltage increment, and therefore it is likely that the system will fail to repeatedly subject the different cells to the same test conditions.

Accordingly, it is an object of the present invention to provide a method and apparatus for particle analysis and cell differentiation, such as hematological analysis, which overcomes the above-described drawbacks and disadvantages of the prior art.

SUMMARY OF THE INVENTION

The present invention is directed to a method and apparatus for differentiating cells in an automated particle analyzer by measuring apparent cell size (or volume), membrane integrity and intracellular complexity. The cells are suspended in a selected reagent mixture including an electrolytic fluid, such as diluent, and if necessary, one or more selected membrane-modifying agents. A predetermined dc voltage is applied across a sensing orifice of the particle analyzer to thereby create a dc electric field across the orifice, and the reagent mixture is passed through the predetermined electric field of the orifice. The change in at least one property of the dc electric field is measured in response to the passage of each of a plurality of cells therethrough, and based on the measured change, a signal is generated for each cell which is indicative of the apparent size (or volume), membrane integrity and intracellular complexity of that cell. A visual display, such as an alphanumeric and/or graphical display, is then generated based on the signals for differentiating the cells.

In a preferred embodiment of the invention, the predetermined voltage is within the range of approximately 20 through 30 volts dc, which has been determined to be sufficient to generate signals indicative of apparent size (or volume), membrane integrity and intracellular complexity for a variety of cell types and/or species of interest. More specifically, a predetermined dc voltage of approximately 20 volts has been determined suitable for nucleated cells subjected to selected membrane-modifying agents, and a predetermined voltage of approximately 30 volts has been determined suitable for non-nucleated cells not subjected to membrane-modifying agents. Also in the preferred embodiment, the at least one property of the electric field measured is the magnitude of the change in dc current caused by passage of each cell through the electric field.

Preferably, the structures of certain cell membranes are selectively altered by employing select membrane-modifying agents, such as lysing agents, detergents or other surfactants, in order to enhance the structural differences of the different cell types (by, for example, increasing the permeability of select cell membranes and/or reducing the structural or "membrane integrity" of select membranes).

One advantage of the present invention is that the predetermined dc voltage of the electric field is sufficient to cause the signal generated upon passage of each cell through the field to include components indicative of apparent cell size (or volume), membrane integrity and intracellular complexity. Accordingly, in contrast to the prior art instruments employing, for example, both dc and rf current sources, or one or both of such sources in combination with a laser source, the method and apparatus of the invention require only a single dc source to generate a signal for each cell indicative of cell size, membrane integrity and intracellular complexity, and thereby provide a single electrical signal enabling differentiation between cells of the same size having a different membrane integrity and/or intracellular complexity.

Other advantages of the present invention will become apparent in view of the following detailed description and accompanying drawings.

DETAILED DESCRIPTION OF THE PREFERRED EMBODIMENT

Figure 1:
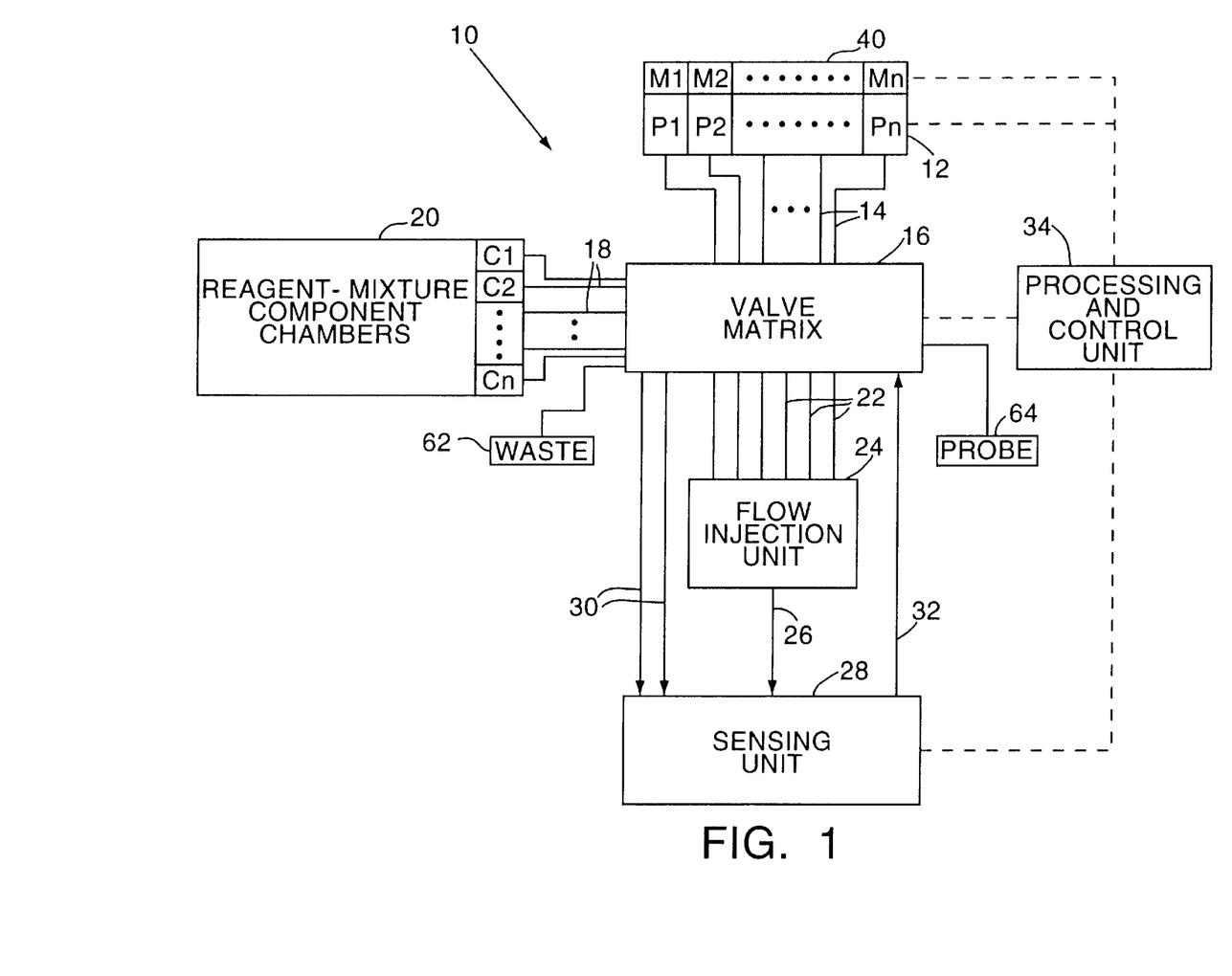
FIG. 1 is a block diagram of an apparatus embodying the present invention.

In FIG. 1, an apparatus embodying the present invention is indicated generally by the reference numeral 10. The apparatus 10 comprises a plurality of pump units 12, indicated schematically in FIG. 1 as P1, P2 . . . Pn, which are coupled in fluid communication through a plurality of pump lines 14 to a valve matrix 16. The valve matrix 16 is of a type known to those of ordinary skill in the pertinent art and connects the various fluid-handling components of the apparatus in fluid communication with each other to control the direction and flow of reagent-mixture components and other fluids, if necessary. The valve matrix 16 is in turn connected through a plurality of lines 18 to a bank of reagent-mixture component chambers 20, indicated schematically in FIG. 1 as C1, C2 . . . Cn. Each chamber 20 is adapted to receive a respective reagent-mixture component, such as a whole blood sample, diluent, membrane-modifying reagent, or diluted blood sample. If necessary, one or more chambers 20 may contain other fluids to be used, for example, to rinse or wash conduits and other fluid-handling components of the apparatus.

The valve matrix 16 is also connected through a plurality of injection lines 22 to a flow-injection unit 24 for injecting at least one reagent-mixture component into a stream of at least one other reagent-mixture component in order to immediately thoroughly and uniformly mix the components and create a selected reagent mixture. The flow injection unit 24, and a preferred method of forming the reagent mixtures, are disclosed in further detail co-pending U.S. patent application Ser. No. 08/458,701, filed Jun. 2, 1995, entitled "Apparatus And Method For Mixing Fluids For Analysis", which is assigned to the Assignee of the present invention, and is hereby expressly incorporated by reference as part of the present disclosure.

The flow injection unit 24 is coupled through a reagent-mixture injection line 26 to a sensing unit 28 defining a sensing orifice for receiving the reagent-mixture. As described in further detail below, the sensing unit 28 applies a predetermined dc voltage across the sensing orifice to thereby create a dc electric field, and is responsive to passage of the sample cells through the orifice to sense a change in at least one property of the dc electric field, and in turn generate based thereon for each cell a signal indicative of the size, membrane integrity and intracellular complexity of the respective cell.

One or more secondary injection/aspiration lines 30 are coupled between the valve matrix 16 and sensing unit 28 for pumping other fluids to the sensing unit, including, for example, diluent sheaths surrounding the reagent-mixture stream. One or more return lines 32 are also coupled between the sensing unit 28 and valve matrix 16 for receiving fluids from the sensing unit, including, for example, the reagent mixture and diluent sheath surrounding the reagent mixture.

As also shown in FIG. 1, a processing and control unit 34 is coupled to each of the pump units 12, the valve matrix 16 and sensing unit 28 to control operation of each component, analyze the data, and provide analysis results. The processing and control unit 34 is preferably constructed to operate in accordance with the teachings of U.S. Pat. Nos. 5,187,673 and 5,349,538, both of which are assigned to Edward L. Carver, Jr., and are hereby expressly incorporated by reference as part of the present disclosure.

The sensing unit 28 is preferably of the type disclosed in U.S. Pat. No. 5,380,491, entitled "Apparatus For Pumping And Directing Fluids For Hematology Testing", and U.S. Pat. No. 5,728,315, which is a divisional of U.S. Pat. No. 5,380,491, both of which are assigned to the Assignee of the present invention, and are hereby expressly incorporated by reference as part of the present disclosure.

Figure 2:
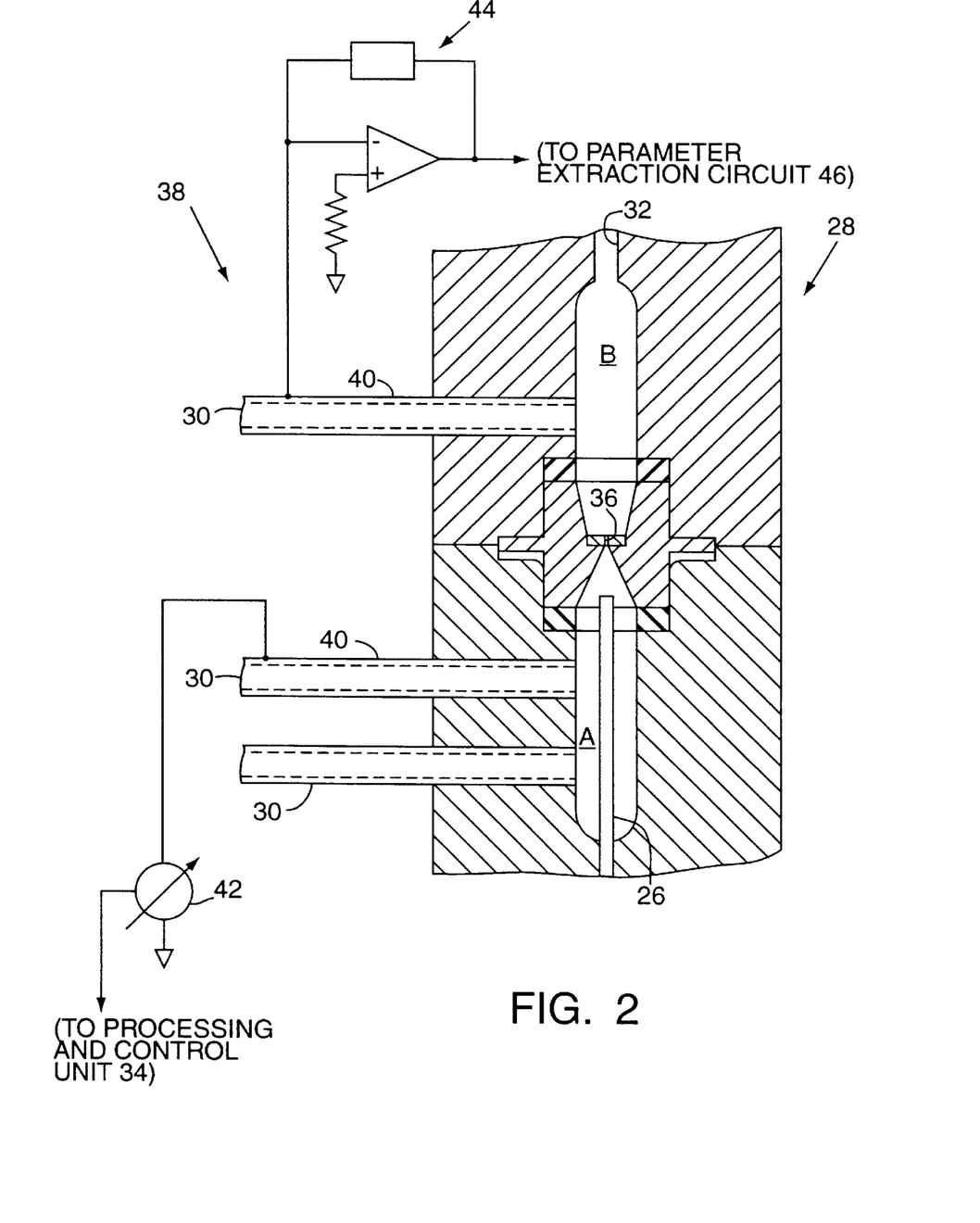
FIG. 2 is a partial schematic, cross-sectional view of a sensing unit comprising a sensing orifice and signal-processing circuitry for generating the signals indicative of apparent cell size, membrane integrity and intracellular complexity.

As shown in FIG. 2, the sensing unit 28 includes a sensing orifice 36 oriented coaxial with the injection line 26 for injecting the reagent mixture through the orifice, and a transducer 38 for generating the signals indicative of cell size, membrane integrity and intracellular complexity. The transducer 38 is formed in part by the conductive ends 40 of the two diluent lines 30 located closest to the sensing orifice 36 and which, in effect, function as electrodes for creating a predetermined dc electric field through and around the sensing orifice. A controllable current source 42 is connected to one of the electrodes 40 for supplying a selected dc current and in turn generating the predetermined dc electric field. An amplifier 44 is connected to the other electrode 40 for generating signals indicative of the change in current flowing between the electrodes in response to the passage of each cell through the sensing orifice and electric field. The amplifier 44 nulls out the predetermined current supplied by the current source 42, and thereby generates and amplifies signals indicative of the changes in current only. Accordingly, and as described further below, the signals generated by the amplifier are indicative of apparent cell size (or volume), membrane integrity and intracellular complexity. As also indicated in FIG. 2, the current source 42 is connected to the processing and control unit 34 for automatically controlling the applied current, and therefore the dc voltage of the electric field as desired, or in accordance with program data for selected cell types and/or species.

In the operation of the apparatus 10, and with reference to FIG. 2, a reagent mixture is injected through the line 26 into the counting orifice 36, and a first diluent sheath is simultaneously injected through one of the secondary lines 30 on the inlet side of the counting orifice surrounding the reagent-mixture stream. Another secondary line 30 is coupled on one end to the outlet side of the counting orifice, and is coupled on the other end through the valve matrix 16 (FIG. 1) to a respective chamber 20 containing diluent for aspirating a second stream of diluent surrounding the reagent-mixture stream on the outlet side of the counting orifice. As disclosed in the above-mentioned patent, the sensing unit 28 preferably includes means for preventing intermixing of the sample or reagent-mixture stream and sheath fluids, including inlet ports for the secondary lines 30 carrying the diluent which are each oriented approximately tangential to a contiguous surface defining either the inlet chamber "A" or outlet chamber "B", respectively, of the sensing unit. As shown in FIG. 2, the reagent-mixture injection line 26 is approximately coaxial with a counting orifice 36 of the sensing unit 28 and injects a narrow stream of the reagent mixture through the center of the orifice.

In accordance with the present invention, a predetermined dc voltage is selected and applied by the electrodes 40 and current source 42 across the sensing orifice 36 to thereby create a dc field within and around the orifice. The reagent mixture containing the suspended cells is then injected through the sensing orifice, a change in at least one property of the dc electric field is measured in response to the passage of each cell therethrough, and an electric signal is generated based thereon for each cell which is indicative of the size, membrane integrity and intracellular complexity of the respective cell. Accordingly, the predetermined dc voltage is selected in accordance with the invention in order to provide a signal, which is based on the measured change in at least one property of the dc electric field upon passage of the respective cell through the field, and is indicative of the apparent size (or volume), membrane integrity and intracellular complexity of the respective cell.

Figure 3:
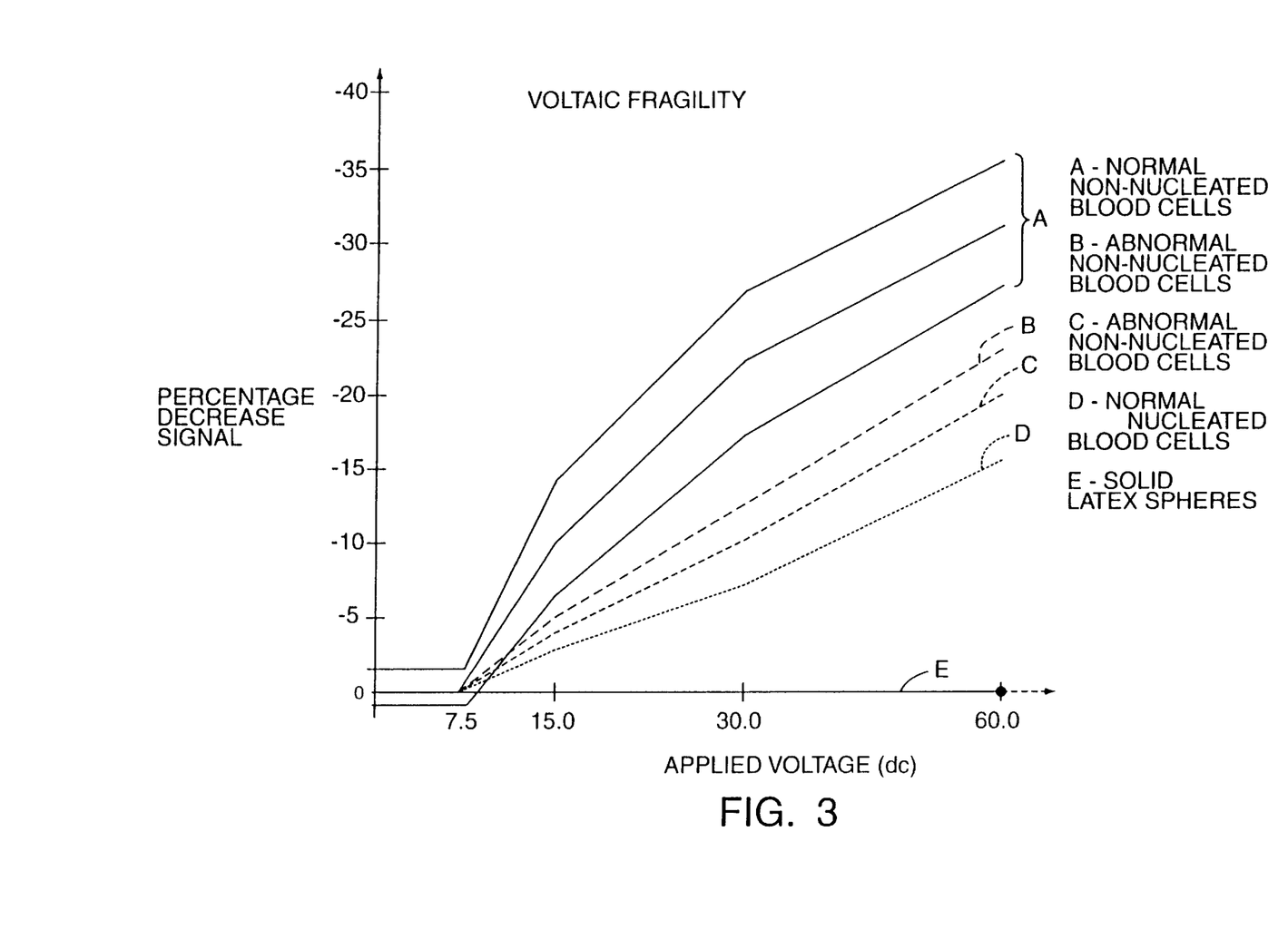
FIG. 3 is a graph illustrating the percentage decrease in signal magnitude versus the applied dc voltage for different cell types.

Turning to FIG. 3, the graph illustrates test data reflecting the percentage decrease in the magnitude of the signals transmitted by the amplifier 44 as compared to the dc voltage of the electric field for various cell types. The solid line curve "A" reflects a range of signatures of various normal, non-nucleated blood cells, the broken line curves "B" and "C" reflect the signatures for different abnormal non-nucleated cells (the curve C reflects a preserved, stabilized blood sample), and the dotted line curve "D" reflects the signature for normal nucleated blood cells. The solid, horizontal line "E" at the base of the graph reflects the data for solid latex spheres.

Based in part on the data of FIG. 3, the present inventors have determined that the predetermined dc voltage should be set between approximately 12.7 and 90 volts. The present inventors have also determined that if the applied voltage is less than approximately 12.7 volts, the signal generated upon passage of a cell through the electric field is indicative of the size or volume of the cell only. However, when the applied voltage is greater than approximately 12.7 volts, the signal generated in response to passage of a cell through the electric field includes components indicative of the size (or volume), membrane integrity and intracellular complexity of that cell. The term "membrane integrity" is used herein to describe the relative fragility of the outer cell membrane and thus its ability to resist the applied voltage. When the applied voltage is greater than about 90 volts dc, the electric noise generated as a result of the increased voltage prevented the inventors from obtaining meaningful and/or useful data.

As further reflected in FIG. 3, when the voltage is closer to the lower end of the above-mentioned range (12.7 volts), the signal generated in response to passage of the cell through the field is indicative to a greater extent of the cell size, as opposed to membrane integrity and intracellular complexity (i.e., the size component of the signal is greater than either the membrane integrity or intracellular complexity components of the signal). When the applied voltage is closer to the upper end of the range (about 60 volts), on the other hand, the signal generated in response to passage of each cell through the field is indicative to a greater extent of the membrane integrity and intracellular complexity, as opposed to the size or volume (i.e., the membrane integrity and intracellular complexity components are greater than the size or volume component of the signal).

In addition, the present inventors have determined, based in part on the analysis of FIG. 3, that for hematological analysis, a predetermined dc voltage of approximately 20 volts is preferred for nucleated blood cells subjected to selected membrane-modifying agents, and a predetermined dc voltage of approximately 30 volts is preferred for non-nucleated blood cells not subjected to membrane-modifying agents. These selected and predetermined applied voltages have been determined to consistently generate signals indicative of the apparent size (volume), membrane integrity, and intracellular complexity for numerous respective cell types of interest.

In the preferred embodiment, the applied voltage was determined by measuring both the resistance across the sensing orifice 36, and the current flowing through the orifice. The resistance was determined by employing a four-wire impedance measurement using a Genrad Model No. 1657 RLC "Digibridge", the current was determined based on the setting of the contollable current source 42, and the product of the measured current and resistance was used to determine the applied voltage.

As will be recognized by those skilled in the pertinent art, although in the preferred embodiment the perturbation of the electric field in response to the passage of each cell therethrough is measured by the change in current flow, this may be equally measured, for example, by sensing the change in voltage or resistance across the orifice in response to the passage of each cell therethrough.

Figure 4:
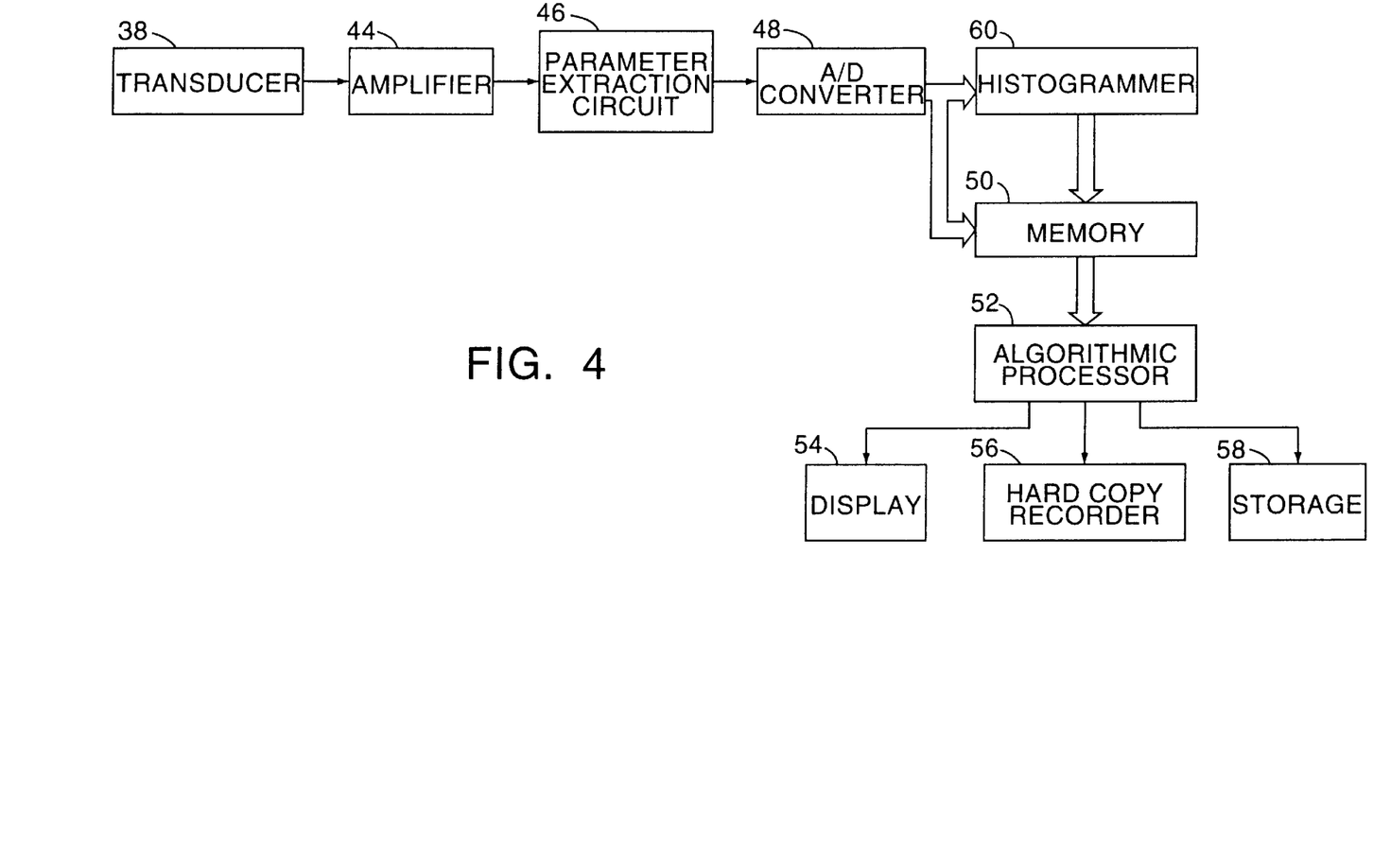
FIG. 4 is block diagram illustrating the signal-processing and display components of the sensing and processing and control units of FIG. 1.

Turning to FIG. 4, and as described above, the amplifier 44 generates amplified signals indicative of the relatively minute changes in current flowing between the electrodes 40 of the transducer, and indicative of the apparent size (or volume), membrane integrity and intracellular complexity of each cell. A parameter extraction circuit 46 receives the amplified signals from the amplifier 44 and measures the desired characteristics of the signal. The pulse height is indicative of the apparent size (or volume), membrane integrity and intracellular complexity, and the pulse width is indicative of the transit time of the respective cell within the electric field ("time of flight") (i.e., the period of time between the point the leading edge of a cell enters the electric field to the point the trailing edge of the cell exits the electric field). The pulse width does not always vary directly or consistently with the pulse height (e.g., less complex cells generally appear to have a lower transit time than more complex cells), and therefore this factor may also be used to facilitate cell identification and discrimination.

An analog to digital (A/D) converter 48 is used to convert the signals processed by the parameter extraction circuit 46 into a digital form suitable for digital processing. The output of the A/D converter is then stored in a memory 50 which records the signal indicative of the respective cell size, membrane integrity and intracellular complexity. An algorithmic processor 52 accesses the contents of the memory 50 and calculates the values for each of cell size, membrane integrity and intracellular complexity using, for example, the computer program set forth in U.S. Pat. Nos. 5,187,673 and 5,349,538 incorporated above. The results of the algorithmic process are then transmitted to a display, which may include a computer monitor or like electronic display unit 54 and a printer or like hard copy recorder or display unit 56, and are also transmitted to a storage device 58 for future retrieval and use. The display may present the information reflected by the signals in any of numerous different formats known to those of ordinary skill in the pertinent art, such as an alphanumeric display, a graphical display or a combination of both. A histogrammer 60 is connected between the A/D converter 48 and the memory 50 to generate histograms in a manner known to those of ordinary skill in the pertinent art.

Also in accordance with the present invention, the reagent mixtures are selected to include, when applicable, membrane-modifying agents, such as select lysing agents, detergents or other surfactants, to selectively alter the integrity of certain cell membranes in order to enhance the differences in the output signals for different cells, and thereby facilitate cell identification and discrimination. It should be noted that the membrane-modifying agents will be employed in lesser quantities than in typical prior art applications in order to alter the membrane integrity without destroying the membrane or perforating the membrane in a manner which will cause cytoplasm leakage.

Exemplary reagent-mixture components, along with the preferred methods for employing these components and for optimizing the reagent mixtures for different species and/or cell types within a particular species, are disclosed in U.S. Pat. No. 5,262,329, entitled "METHOD FOR IMPROVED MULTIPLE SPECIES BLOOD ANALYSIS", dated Nov. 16, 1993, U.S. Pat. No. 5,316,725, entitled "REAGENT SYSTEM FOR THE IMPROVED DETERMINATION OF WHITE BLOOD CELL SUBPOPULATIONS", dated May 31, 1994, and U.S. Pat. No. 5,316,951, entitled "METHOD FOR THE IMPROVED DETERMINATION OF WHITE BLOOD CELL SUBPOPULATIONS", dated May 31, 1994, which are each assigned to Edward L. Carver, Jr., and are hereby expressly incorporated by reference as part of the present disclosure. The method for optimizing the reagent mixtures disclosed in these patents may equally be employed for determining the selected reagent mixtures for use in the apparatus and method of the present invention.

The processing and control unit 34 also preferably has a database of information pertaining to the predetermined reagent-mixture ratios and applied voltage levels for selected species (e.g., human, dog, cat, rat, mouse, horse, cow, rabbit, monkey, pig, goat, bird or bird-type, etc.), and if desired, for selected conditions associated with each species. Accordingly, an operator may input through a keyboard or other input device for the control unit 34 the particular animal species, or if necessary, a specific reagent-mixture ratio or applied voltage level that may not otherwise be in the database. The processing and control unit 34 is responsive to this input to adjust the controllable current source 42 to the corresponding selected voltage level, and to control a plurality of the pump motors 40 to drive the respective pump units 12 to aspirate from the reagent-mixture chambers 20 into each pump a predetermined volume of a respective reagent-mixture component corresponding to the selected reagent-mixture ratio. The control unit 34 also aspirates a predetermined volume of diluent from a diluent chamber 20 into a respective pump unit 12 for injecting the diluent sheath surrounding the reagent-mixture stream.

The processing and control unit 34 operates the pump motors 40 to simultaneously inject each of the selected reagent-mixture components into the flow-injection unit 24 (FIG. 1) to thoroughly and uniformly mix the components and create the selected reagent mixture. As more specifically described in the above-mentioned co-pending patent application, the flow rate of each reagent-mixture component may be set by the control unit 34 so that the flow-rate ratio is the same as the desired reagent-mixture ratio. For example, if the desired reagent-mixture ratio is 1000 $\mu$l diluent:60 $\mu$l membrane-modifying agent A:20 $\mu$l blood, then the flow rates for these selected reagent-mixture components are set at a ratio of 1000:60:20, respectively. The flow-rate ratios are preferably set by adjusting the speed of each pump motor to achieve the respective flow rates and thereby achieve the selected mixture ratio.

The selected reagent-mixture components are then simultaneously injected into the flow-injection unit 24 at the selected flow-rate ratio. The reagent-mixture components are preferably simultaneously injected and mixed in the flow-injection unit 24, and the resultant reagent mixture is in turn injected through the reagent-mixture injection line 26 and into the sensing unit 28. The substantially steady-state flow of the positive-displacement pumps injecting the reagent mixture through the flow-injection unit 24 and into the sensing unit 28, in combination with the smooth-walled configuration of the flow-injection line 26 and sensing unit, facilitates in creating a substantially laminar flow as the reagent mixture enters the sensing orifice. The control unit also simultaneously injects a first diluent sheath surrounding the reagent-mixture stream on the inlet side of the counting orifice, and aspirates a second diluent sheath on the outlet side of the counting orifice through the secondary lines 30 to facilitate maintaining a uniform, concentric and steady-state flow of reagent mixture through the counting orifice. Upon passage through the sensing unit, the reagent mixture is aspirated into the return line 32 by an additional pump unit 12 and is ultimately discharged into the waste chamber 62.

As also shown in FIG. 1, the apparatus 10 may further comprise a probe 64 coupled to the valve matrix 16 for aspirating the various fluids through the valve matrix and introducing the fluids into the various reagent-mixture component chambers 20. The waste chamber 62 is also coupled to the valve matrix 16 for receiving the fluids after passage through the sensing unit 28, and any other fluids in the apparatus to be discarded as waste.

Each of the pump units 12 is preferably a positive-displacement pump, such as a syringe pump, as shown, for example, in U.S. Pat. No. 5,380,491. As shown in FIG. 1, each pump unit 12 is preferably independently driven by a respective pump motor 40, illustrated schematically as M1, M2 . . . Mn, and each pump motor is coupled to the processing and control unit 34. Accordingly, each pump unit 12 can be independently actuated and controlled by the processing and control unit 34, to in turn independently control the flow rates of the fluids being injected or aspirated by the pumps. Each pump motor 40 may be a step motor, or other DC or AC motor with proper feedback and electronic control in order to precisely control actuation of the motor and respective pump, and in turn precisely control the volumes and flow rates of the fluids being pumped.

As will be recognized by those skilled in the pertinent art, numerous changes and modifications may be made to the above-described and other embodiments of the present invention, without departing from its scope as defined in the appended claims. Accordingly, this detailed description of a preferred embodiment is to be taken in an illustrative, as opposed to a limiting sense.

What is claimed is:

1. A method for differentiating a plurality of cells in an automated particle analyzer, wherein each of the plurality of cells differs from another in at least one of cell size, membrane integrity and intracellular complexity, comprising the following steps:

suspending the cells in an electrolytic fluid;

applying a predetermined dc voltage across a sensing orifice of the particle analyzer and thereby creating a dc electric field across the orifice;

passing the suspended cells through the dc electric field of the sensing orifice;

sensing a change in magnitude in at least one of electric current, resistance and voltage of the dc electric field in response to the passage of each of a plurality of cells therethrough, and generating based thereon for each cell a respective electric signal indicative of the change in magnitude in at least one of the electric current, resistance and voltage of the dc electric field in response to the passage of the respective cell therethrough;

selecting the predetermined voltage of the dc electric field so that the electric signal generated upon passage of each of the plurality of cells through the dc electric field is indicative of the size, membrane integrity and intracellular complexity of the respective cell; and generating a visual display of graphic indicia corresponding to a plurality of the signals for differentiating the cells based thereon.

2. A method as defined in claim 1, wherein the predetermined dc voltage is within the range of approximately 12.7 volts and approximately 90 volts.

3. A method as defined in claim 2, wherein the cells are selected from the group including nucleated blood cells and non-nucleated blood cells and the predetermined dc voltage is within the range of approximately 20 volts dc through approximately 30 volts dc.

4. A method as defined in claim 1, wherein the step of sensing a change in at least one property of the dc electric field includes sensing the change in electric current flowing through the electric field.

5. A method as defined in claim 1, further comprising the step of adding at least one membrane-modifying agent to the cell suspension to selectively alter the membrane integrity of at least one selected cell type without perforating a membrane and causing leakage of an internal cell substance of the selected cell type.

6. A method as defined in claim 2, further comprising the step of decreasing the predetermined dc voltage within said range to thereby increase the magnitude of a size component of the generated signal in comparison to the magnitude of a membrane integrity component and the magnitude of an intracellular complexity component of the generated signal.

7. A method as defined in claim 2, further comprising the step of increasing the predetermined dc voltage within said range to thereby increase the magnitude of a membrane integrity component and the magnitude of an intracellular complexity component of the generated signal in comparison to the magnitude of a size component of the generated signal.

8. A method as defined in claim 1, further comprising the step of generating a database of a plurality of different predetermined dc voltages for differentiating cells of each of a plurality of different animal species, and wherein each predetermined dc voltage corresponds to at least one respective animal species.

9. An apparatus for differentiating a plurality of cells suspended in an electrolytic fluid in an automated particle analyzer, wherein each of the plurality of cells differs from another in at least one of cell size, membrane integrity and intracellular complexity, comprising:

means for applying a predetermined dc voltage across a sensing orifice of the particle analyzer and creating a dc electric field across the orifice;

means for passing the suspended cells through the dc electric field of the sensing orifice;

means for sensing a change in magnitude in at least one of electric current, resistance and voltage of the dc electric field in response to the passage of each of a plurality of cells therethrough, and generating based thereon for each cell a respective electric signal indicative of both the change in magnitude of at least one of the electric current, resistance and voltage of the dc electric field in response to the passage of the respective cell therethrough, and the size, membrane integrity and intracellular complexity of the respective cell; and means for generating a visual display based on the signals for differentiating the cells.

10. An apparatus as defined in claim 9, wherein the predetermined dc voltage is within the range of approximately 12.7 volts and approximately 90 volts.

11. An apparatus as defined in claim 10, wherein the cells are selected from the group including nucleated blood cells and non-nucleated blood cells and the predetermined dc voltage is within the range of approximately 20 volts dc through approximately 30 volts dc.

12. An apparatus as defined in claim 9, wherein the means for sensing a change in at least one property of the dc electric field senses a change in current flowing through the electric field.

13. An apparatus as defined in claim 9, further comprising means for adding at least one membrane-modifying agent to the cell suspension to selectively alter the membrane integrity of at least one selected cell type without perforating a membrane and causing leakage of an internal cell substance of the selected cell type.

14. An apparatus as defined in claim 10, further comprising means for decreasing the predetermined dc voltage within said range to thereby increase the magnitude of a size component of the generated signal in comparison to the magnitude of a membrane integrity component and the magnitude of an intracellular complexity component of the generated signal.

15. An apparatus as defined in claim 10, further comprising means for increasing the predetermined dc voltage within said range to thereby increase a membrane integrity component and an intracellular complexity component of the generated signal in comparison to a size component of the generated signal.

16. An apparatus as defined in claim 9, further comprising a database of a plurality of different predetermined dc voltages for differentiating cells of each of a plurality of different animal species, wherein each predetermined dc voltage corresponds to at least one respective animal species.

17. An apparatus as defined in claim 16, further comprising a database of a plurality of predetermined reagent-mixtures for differentiating cells of each of a plurality of different animal species, wherein each predetermined reagent mixture corresponds to at least one respective animal species.

18. An apparatus for differentiating a plurality of cells suspended in an electrolytic fluid in an automated particle analyzer, wherein each of the plurality of cells differs from another in at least one of cell size, membrane integrity and intracellular complexity, comprising:

a sensing orifice;

at least two electrodes electrically coupled across the sensing orifice;

at least one of a voltage source and a current source electrically coupled to the electrodes which applies a predetermined dc voltage to the electrodes and, in turn, creates a predetermined dc electric field across the orifice, and wherein the predetermined dc voltage is selected so that a perturbation of the dc electric field upon passage of each of the plurality of cells therethrough is indicative of cell size, membrane integrity and intracellular complexity of the respective cell;

at least one fluid conduit coupled in fluid communication with the sensing orifice which introduces the plurality of cells suspended in the electrolytic fluid through the dc electric field of the sensing orifice;

an electric circuit coupled to the electrodes which senses a change in magnitude in at least one of electric current, resistance and voltage of the dc electric field in response to the passage of each of a plurality of cells therethrough, and generates based thereon for each cell a respective electric signal indicative of both (i) the change in magnitude of at least one of the electric current, resistance and voltage of the dc electric field in response to the passage of the respective cell therethrough, and (ii) the size, membrane integrity and intracellular complexity of the respective cell; and a display unit coupled to the electric circuit and which generates a visual display based on the signals for differentiating the cells.

19. An apparatus as defined in claim 18, wherein the electric circuit includes an amplifier electrically coupled to at least one electrode, which substantially nulls out the current of the dc electric field flowing through the electrode, and thereby generates signals indicative of changes in magnitude of current of the dc electric field upon passage of each cell therethrough.

20. An apparatus as defined in claim 18, comprising an adjustable current source electrically coupled to the electrodes, and which applies any of a plurality of different predetermined dc currents to the electrodes to, in turn, generate any of a plurality of dc electric fields within the range of approximately 12.7 and 90 volts.

* * * * *